United States Patent
Eisenbach-Schwartz et al.

(10) Patent No.: US 7,351,686 B2
(45) Date of Patent: *Apr. 1, 2008

(54) METHOD FOR NEURONAL PROTECTION IN AMYOTROPHIC LATERAL SCLEROSIS BY A VACCINE COMPRISING COPOLYMER-1 OR COPOLYMER-1 RELATED PEPTIDES

(75) Inventors: Michal Eisenbach-Schwartz, Rehovot (IL); Esther Yoles, Nahal Soreq (IL); Jonathan Kipnis, Modiin (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/485,576

(22) PCT Filed: Dec. 5, 2002

(86) PCT No.: PCT/IL02/00979

§ 371 (c)(1),
(2), (4) Date: Oct. 27, 2004

(87) PCT Pub. No.: WO03/047500

PCT Pub. Date: Jun. 12, 2003

(65) Prior Publication Data

US 2005/0220802 A1    Oct. 6, 2005

Related U.S. Application Data

(60) Provisional application No. 60/336,139, filed on Dec. 6, 2001.

(51) Int. Cl.
*A61K 38/00* (2006.01)
*A61K 39/00* (2006.01)
*G01N 33/53* (2006.01)

(52) U.S. Cl. .................. 514/2; 424/185.1; 436/547
(58) Field of Classification Search .................. None
See application file for complete search history.

(56) References Cited

U.S. PATENT DOCUMENTS 3,849,550 A   11/1974  Teitelbaum et al.
5,800,808 A   9/1998   Konfino et al.
6,800,285 B2 * 10/2004 Rodriguez et al. ....... 424/133.1
6,844,314 B2 * 1/2005 Eisenbach-Schwartz et al. .................. 514/2
2002/0037848 A1  3/2002 Eisenbach-Schwartz et al.
2002/0072493 A1  6/2002 Eisenbach-Schwartz et al.
2003/0003082 A1 * 1/2003 Eisenbach-Schwartz et al. .................. 424/93.7
2003/0108528 A1  6/2003 Eisenbach-Schwartz et al.
2004/0248802 A1 * 12/2004 Eisenbach-Schwartz et al. .................. 514/12
2004/0253218 A1  12/2004 Eisenbach-Schwartz et al.
2005/0159336 A1 * 7/2005 Eisenbach-Schwartz et al. .................. 514/2

FOREIGN PATENT DOCUMENTS

WO    9934827 A1    7/1999
WO    9960021 A2    11/1999
WO    WO0193893  *  1/2001
WO    0152878 A2    7/2001

OTHER PUBLICATIONS

Bruijn et al. Annu. Rev. Neurosci. 2004, 27: 723-49.*
Rothstein Curr. Opin. In Neurobiol. 1996. 6: 679-687.*
Hem et al. Pharm. Biotechnol. 1995; 6:249-276.*
Mosonego et al. Science 2003. 302: 834-838.*
Watase et al. Nat Rev. Genet. 2003. 4: 296-307.*
Sela et al. (Vaccine 1992. 10: 991-999).*
J. Kipnis et al, "Vaccination With a Safe MBP-Crossreactive Peptide as a Possible Treatment for CNS Injuries", 2000, vol. 17, No. 10, p. 991.

* cited by examiner

*Primary Examiner*—Christine Saoud
*Assistant Examiner*—Chang-Yu Wang
(74) *Attorney, Agent, or Firm*—Browdy and Neimark, PLLC

(57) ABSTRACT

A vaccine for reducing disease progression, and/or protection of motor nerve degeneration, and/or protection from glutamate toxicity in motor neurone disease (MND), particularly amyotrophic lateral sclerosis (ALS), patients, comprising an active agent selected from the group consisting of Cop 1, a Cop 1-related peptide, a Cop 1-related polypeptide, and poly-Glu, Tyr. The active agent is preferably Cop 1 or poly-Glu, Tyr, and can be administered with or without an adjuvant.

11 Claims, 9 Drawing Sheets

METHOD FOR NEURONAL PROTECTION IN AMYOTROPHIC LATERAL SCLEROSIS BY A VACCINE COMPRISING COPOLYMER-1 OR COPOLYMER-1 RELATED PEPTIDES

FIELD AND BACKGROUND OF INVENTION

The present invention relates to a vaccine and methods for the treatment of Motor Neurone Diseases (MND), particularly amyotrophic lateral sclerosis (ALS).

Motor Neurone Disease (MND) is the name given to a group of related diseases affecting the motor neurones in the brain (upper motor neurons) and spinal cord (lower motor neurons). Motor neurones (or motor neurons) are the nerve cells along which the brain sends instructions, in the form of electrical impulses, to the muscles. Degeneration of the motor neurones leads to weakness and wasting of muscles. This generally occurs in arms or legs initially, some groups of muscles being affected more than others.

There are several classifications of MND. In most cases of MD, degeneration of both the upper and lower motor neurones occurs. This condition is called Amyotrophic Lateral Sclerosis (ALS), also known as Lou Gehrig's disease, and is characterized by muscle weakness, stiffness and fasciculations (muscle twitching). There are also less common forms in which a more selective degeneration of either the upper motor neurones (such as Primary Lateral Sclerosis, PLS) or lower motor neurones (such as Progressive Muscular Atrophy, PMA) is observed. Progressive Bulbar Palsy (PBP or Bulbar Onset) is a version of ALS that starts with difficulties in swallowing, chewing and speaking and affects approximately 25% of ALS patients.

There is considerable overlap between these forms of MND. People with PMA in time develop upper motor neurone involvement and in both PMA and ALS some people may eventually experience speech and swallowing difficulties in varying degrees (bulbar onset ALS or PMA).

ALS, is a chronic, progressive neurodegenerative disease characterized by gradual degeneration of the nerve cells in the central nervous system (CNS) that control voluntary muscle movement. The progressive loss of motor neurons leads to gradual skeletal muscle atrophy and to inevitable death, usually within 2-3 to ten years of the disease onset. Muscular weakness and atrophy and signs of anterior horn cell dysfunction are initially noted most often in the hands and less often in the feet. The site of onset is random, and progression is asymmetric. In the U.S.A. alone, 30,000 people currently have ALS and about 8,000 new cases are diagnosed each year.

ALS occurs in sporadic (SALS) and familial (FALS) forms (Mulder et al., 1986; Munsat, 1989). The primary risk factors are mostly unknown, yet 5 to 10% of all ALS patients are familial (FALS). About 20% of all familial forms were found to have mutations in the gene encoding Cu/Zn superoxide dismutase type 1 on chromosome 21 (Rosen et al., 1993; Brown, 1995). SOD is an enzyme that catalyzes the conversion of superoxide anions to hydrogen peroxide, and thus SOD can protect cells against the deleterious effects of these toxic radicals. It appears that the toxicity of different SOD mutants is not due to decreased free-radical scavenging activity since no correlation was found between enzymatic activity, polypeptide half-life and resistance to proteolysis with age of onset or rapidity of human disease progression (for review, see Julien, 2001). Transgenic mice expressing various SOD1 mutants developed motor neuron disease and thus constitute an accepted animal model for testing ALS and other motor neurone therapies.

Recently, a new ALS gene has been identified by two independent groups of scientists (Hadano et al., 2001; Yang et al., 2001). This new gene, called ALS2, is located on chromosome 2 and encodes for a protein named alsin. The new ALS2 gene is mutated in both people with juvenile amyotrophic lateral sclerosis (JALS), also known as ALS2, and people with juvenile primary lateral sclerosis (JPLS). Mutations in different regions of the chromosome are associated with different motor neuron diseases. Specifically, a mutation in one region is found in people with ALS, while mutations in two other regions are found in people with JPLS. In the future, transgenic mice carrying these mutations will certainly constitute a further model for testing ALS therapies.

Numerous studies over the last decade have been devoted to understanding the etiology, prognosis and progression of the disease. No consensus has been reached, except for admitting that it is a multi-factorial disease in terms of circumstances leading to its progression, while the etiology remains unclear.

It is evident today that many of the factors which contribute to the progression of ALS are found in many other chronic and acute neurodegenerative disorders. These factors include oxidative stress, excitotoxicity, deprivation of trophic support, and ionic imbalance. Over the years attempts have been made to halt the progression of ALS, as in other chronic and acute neurodegenerative disorders, by blocking different mediators of cytotoxicity. Most of these clinical trials have had negative results (Turner et al., 2001).

Oxidative stress is characterized by accumulation of free radicals that can lead to motor neuron death. Free radicals damage components of the cells' membranes, proteins or genetic material by "oxidizing" them. These free radicals may be generated when the enzyme SOD malfunctions, either because of genetic mutation as occurs in some familial ALS patients or because of the chemical environment of the nerve cells, or they may be generated as a result of glutamate excitotoxicity, or for some other reason. Many ALS patients take Coenzyme Z Q10 and Vitamin E in all effort to neutralize free radicals.

Glutamate is one of the most common mediators of toxicity in acute and chronic degenerative disorders (Pitt et al., 2000) like status epilepticus, cerebral ischemia, traumatic brain injury, ALS, Huntington's chorea, lathyrisms and Alzheimer's disease. Glutamate is a primary excitatory neurotransmitter in the human CNS. L-glutamate is present at a majority of synapses and is capable of displaying dual activity: it plays a pivotal role in normal functioning as an essential neurotransmitter, but becomes toxic when its physiological levels are exceeded.

For spinal motor neurons, rapid glutamate removal following synaptic activity is accomplished by the glutamate transporter EAAT2 present in astrocytes. Decrease in EAAT2 activity and protein level was found in brain tissue of ALS patients (Rothstein et al., 1992), This could lead to increased extracellular concentration of glutamate and death of motor neurons. Clinically, the beneficial effect of Riluzole, a glutamate release inhibitor, on the course of the disorder in both humans and transgenic mice, led to the approved drug treatment of ALS. However, in neutralizing the toxic effect it is likely to interfere with the physiological functioning of glutamate as a ubiquitous CNS neurotransmitter.

The role of immune factors, cellular and molecular, in ALS has been debated over the years. It has been argued, as in many other neurodegenerative diseases, that inflammation is associated with the disease propagation, and the usage of immunosuppressive drugs in ALS has been suggested. Also, in many ALS patients, a correlation was observed with the presence of anti-ganglioside antibodies, which led some researchers to suggest that ALS is an autoimmune disease. However, no conclusive evidence has been provided to support this hypothesis.

In the laboratory of the present inventors, it has been recently observed that under neurodegenerative conditions caused by mechanical (axotomy) or biochemical (glutamate, oxidative stress) insults, the immune system plays a critical role. Thus, it has been found that activated T cells that recognize an antigen of the nervous system (NS) promote nerve regeneration or confer neuroprotection. Reference is made to PCT Publication No. WO 99/60021, the entire contents of which is hereby incorporated herein by reference. More specifically, T cells reactive to MBP were shown to be neuroprotective in rat models of partially crushed optic nerve (Moalem et al, 1999) and of spinal cord injury (Hauben et al, 2000). Until recently, it had been thought that the immune system excluded immune cells from participating in nervous system repair. It was quite surprising to discover that NS-specific activated T cells could be used to promote nerve regeneration or to protect nervous system tissue from secondary degeneration which may follow damage caused by injury or disease of the CNS or peripheral nervous system (PNS).

It was further observed by the present inventors that stressful conditions in the CNS harness the adaptive immune response to cope with the stress and that this response is genetically controlled. Thus, the survival rate of retinal ganglion cells in adult mice or rats after crush injury of the optic nerve or intravitreal injection of a toxic dosage of glutamate was shown to be up to two-fold higher in strains that are resistant to CNS autoimmune diseases than in susceptible strains. The difference was found to be attributable to a beneficial autoimmune T cell response that was spontaneously evoked after CNS insult in the resistant but not in susceptible strains. Thus, the survival rate of neurons as a result of such an insult is higher when T cell response directed against self is evoked, provided that it is well-regulated. In other words, it was demonstrated that a protective autoimmune response is evoked to oppose the stressful conditions so as to protect the animal from the insult consequences. It was further observed that in animals with an impaired ability to regulate such a response, or in animals devoid of mature T cells (as a result of having undergone thymectomy at birth), the ability to cope with the stressful conditions is reduced. Consequently, the survival rate of neurons following CNS insult in these animals is significantly lower than in animals endowed with an effective mechanism for mounting protective autoimmune T cell-mediated response (Kipnis et al., 2001).

It was then further found by the present inventors that vaccination with non-pathogenic synthetic copolymers that resemble self-proteins such as Copolymer 1 (Cop 1 or Glatiramer), a random copolymer composed of the four amino acids: tyrosine-glutamate-alanine-lysine (hereinafter "Cop 1"), and poly-Glu, Tyr (hereinafter "PolyYE"), and by T cells activated thereby, after traumatic CNS insult can be used to boost the protective autoimmunity and thereby to reduce further injury-induced damage, and can further protect CNS cells from glutamate toxicity. Reference is made to our previous U.S. patent application Ser. Nos. 09/756,301 and 09/765,644, both dated 22 Jan. 2001, herein incorporated by reference in their entirety as if fully disclosed herein, corresponding to WO 01/93893, which disclose that Cop 1, Cop 1-related peptides and polypeptides and T cells activated therewith protect CNS cells from glutamate toxicity (U.S. Ser. No. 09/756,301) and prevent or inhibit neuronal degeneration or promote nerve regeneration in the CNS or PNS (U.S. Ser. No. 09/765,644). Reference is further made to our previous U.S. patent application Ser. No. 09/893,344 dated 28 Jun. 2001, herein incorporated by reference in its entirety as if fully disclosed herein, which discloses that the copolymer poly-Glu$^{50}$Tyr$^{50}$, formerly called polyGT and also designated PolyYE, and T cells activated therewith, protect CNS cells from glutamate toxicity and also prevent or inhibit neuronal degeneration or promote nerve regenetion in the CNS or PNS. Specifically, it was shown in said applications that in optic nerve fibers, the number of surviving retinal ganglion cells was significantly higher in the Cop 1-immunized or poly-Glu, Tyr-immunized mice than in the mice injected with PBS.

The sole drug approved and currently available for treatment of ALS is Riluzole (2-amino-6-(trifluoromethoxy) benzothiazole), a putative blocker of glutamate release, which appears to have some spasm-reducing effects in this condition, possibly through inhibition of glutamatergic transmission in the CNS. It is administered orally in the form of tablets. Riluzole does not cure the disease or improve symptoms. It exerts a modest to significant effect in ALS patients by elongating their life span for about 3 months, but does not improve muscular strength or neurologic function.

It would be highly desirable to provide further medicaments for the treatment of motor neuron diseases, including ALS.

Citation or identification of any reference in this section or any other part of this application shall not be construed as an admission that such reference is available as prior art to the invention.

SUMMARY OF THE INVENTION

It has now been found, in accordance with the present invention, that immunization with Cop 1 can protect transgenic mice overexpressing human SOD1 and mice after facial nerve axotomy, both models for ALS, from motor neuron degeneration. This and the fact that both Cop 1 and PolyYE are effective in protecting retinal ganglion cells from glutamate toxicity, indicates the suitability of these copolymers for the treatment of motor neurone diseases, particularly ALS.

The present invention thus relates, in one aspect, to a method for reducing disease progression, for protection of motor neuron degeneration and/or for protection from glutamate toxicity in a patient suffering from a motor neurone disease (MND), which comprises immunizing said patient with a vaccine comprising an active agent selected from the group consisting of Cop 1, a Cop 1-related peptide, a Cop 1-related polypeptide, and PolyYE.

The motor neurone disease (MND) is any disease affecting the motor neurones in the brain and spinal cord and includes amyotrophic lateral sclerosis (ALS), both familial (FALS) and sporadic (SALS) ALS, primary lateral sclerosis (PLS), progressive muscular atrophy (PMA), progressive bulbar palsy (PBP or bulbar onset), and combined forms thereof such as bulbar onset ALS and bulbar onset PMA.

In one embodiment, the method of the invention includes treatment also with Riluzole or any other drug suitable for treatment of MND, particularly ALS.

In another aspect, the present invention provides a vaccine for reducing disease progression, for protection of motor nerve degeneration and/or for protection from glutamate toxicity in a motor neurone disease (MND), particularly ALS, comprising an active agent selected from the group consisting of Cop 1, a Cop 1-related peptide, a Cop 1-related polypeptide, and poly-Glu, Tyr.

In a further aspect, the present invention relates to the use of an active agent selected from the group consisting of Cop 1, a Cop 1-related peptide, a Cop 1-related polypeptide, and poly-Glu, Tyr, for the manufacture of a vaccine for reducing disease progression, for protection of motor nerve degeneration and/or for protection from glutamate toxicity in motor neurone disease (ND), particularly ALS.

The active agent may be administered without any adjuvant or it may be emulsified in an adjuvant suitable for human clinical use. The adjuvant suitable for human clinical use is selected from aluminum hydroxide, aluminum hydroxide gel, and aluminum hydroxyphosphate. In a preferred embodiment, the vaccine adjuvant is amorphous aluminum hydroxyphosphate having an acidic isoelectric point and an Al:P ratio of 1:1 (herein referred to as Alum-phos).

In one preferred embodiment, the active agent of the vaccine of the invention is Cop 1. In another preferred embodiment, the active agent is poly-Glu, Tyr.

In addition, the vaccine may be administered in a regimen that includes administration of Riluzole or another drug suitable for treatment of ALS.

BRIEF DESCRIPTION OF THE FIGURES

FIG. 4A shows the average hanging time (seconds) on a rotating vertical rod per week of ALS mice immunized with Cop 1 emulsified in Alum-phos (mice 1, 2 and 4) and of non-immunized transgenic mice (mice 3, 5 and 6). FIG. 4B depicts the average hanging time (% of baseline) of 3 ALS mice immunized with Cop 1 in Alum-phos (black columns) as compared to that of 3 transgenic non-immunized mice (control, gray columns). To compare the rate of disease progression, all the animals were synchronized to the time of onset of muscle weakness (time 0), normalizing each animal hanging time to its own baseline time before the disease onset (baseline time—100%). The figure depicts the average±SEM hanging time per each group, for the following weeks of disease progression.

DETAILED DESCRIPTION OF THE INVENTION

Figure 1:
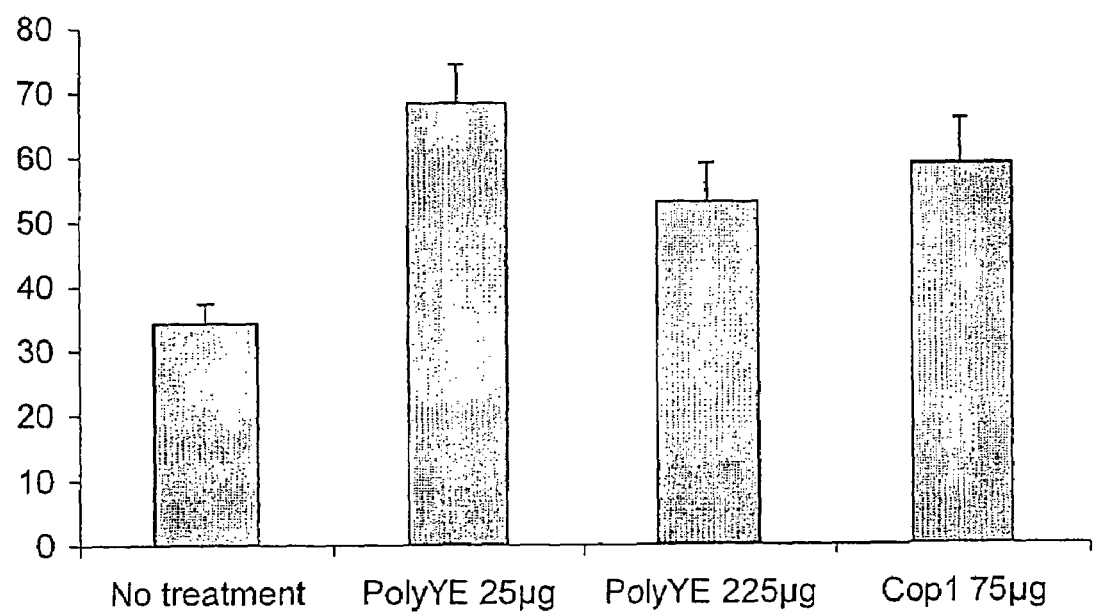
FIG. 1 shows that immunization with Cop 1 or PolyYE without adjuvant protects mice retinal ganglion cells (RGCs) from glutamate toxicity.

The present invention provides a vaccine and a method for reducing disease progression, for protection of motor nerve degeneration, for prolonging life span and improving quality of life, and/or for protection from glutamate toxicity in a patient suffering from MND, particularly ALS, which comprises immunizing said patient with a vaccine comprising an active agent selected from the group consisting of Cop 1, a Cop 1-related peptide, a Cop 1-related polypeptide, or PolyYE, either without adjuvant or emulsified in an adjuvant suitable for human clinical use.

As used herein, the terms "motor neurons" and "motor neurons", the terms "PolyYE" and "poly-Glu, Tyr", and the terms "Cop 1" and "Copolymer 1", are each used interchangeably.

For the purpose of the present invention, "Cop 1 or a Cop 1-related peptide or polypeptide" is intended to include any peptide or polypeptide, including a random copolymer, that cross-reacts functionally with myelin basic protein (MBP) and is able to compete with MBP on the MHC class II in the antigen presentation.

The vaccine of the invention may comprise as active agent a random copolymer comprising a suitable quantity of a positively charged amino acid such as lysine or arginine, in combination with a negatively charged amino acid (preferably in a lesser quantity) such as glutamic acid or aspartic acid, optionally in combination with a non-charged neutral amino acid such as alanine or glycine, serving as a filler, and optionally with an amino acid adapted to confer on the copolymer immunogenic properties, such as an aromatic amino acid like tyrosine or tryptophan. Such vaccines may include any of those copolymers disclosed in WO 00/05250, the entire contents of which being hereby incorporated herein by reference.

More specifically, the vaccine for use in the present invention comprises at least one copolymer selected from the group consisting of random copolymers comprising one amino acid selected from each of at least three of the following groups: (a) lysine and arginine; (b) glutamic acid and aspartic acid; (c) alanine and glycine; and (d) tyrosine and tryptophan.

The copolymers for use in the present invention can be composed of L- or D-amino acids or mixtures thereof. As is known by those of skill in the art, L-amino acids occur in most natural proteins. However, D-amino acids are commercially available and can be substituted for some or all of the amino acids used to make the terpolymers and other copolymers used in the present invention. The present invention contemplates the use of copolymers containing both D- and L-amino acids, as well as copolymers consisting essentially of either L- or D-amino acids.

In one embodiment of the invention, the copolymer contains four different amino acids, each from a different one of the groups (a) to (d). A preferred copolymer according to this embodiment comprises in combination alanine, glutamic acid, lysine, and tyrosine, of net overall positive electrical charge and of a molecular weights of about 2,000-40,000 Da, preferably of about 2,000-13,000 Da, and is most preferably Copolymer 1 of average molecular weight of about 4,700-13,000 Da. Preferred molecular weight ranges and processes for making a preferred form of Cop 1 are described in U.S. Pat. No. 5,800,808, the entire contents of which being hereby incorporated in the entirety. It is clear that this is given by way of example only, and that the vaccine can be varied both with respect to the constituents and relative proportions of the constituents if the above general criteria are adhered to. Thus, the copolymer may be a polypeptide from about 15 to about 100, preferably from about 40 to about 80, amino acids in length, and is preferably the copolymer having the generic name glatiramer acetate.

In another embodiment, the copolymer contains three different amino acids each from a different one of three groups of the groups (a) to (d). These copolymers are herein referred to as terpolymers.

In one embodiment, the terpolymers for use in the present invention contain tyrosine, alanine, and lysine, hereinafter designated YAK. The average molar fraction of the amino acids in these terpolymers can vary. For example, tyrosine can be present in a mole fraction of about 0.005-0.250; alanine can be present in a mole fraction of about 0.3-0.6; and lysine can be present in a mole fraction of about 0.1-0.5. The average molecular weight is between 2,000-40,000 Da, and preferably between about 3,000-35,000 Da. In a more preferred embodiment, the average molecular weight is about 5,000-25,000 Da. It is possible to substitute arginine for lysine, glycine for alanine, and/or tryptophan for tyrosine.

In another embodiment, the terpolymers for use in the present invention contain tyrosine, glutamic acid, and lysine, hereinafter designated YEK. The average molar fraction of the amino acids in these terpolymers can vary: glutamic acid can be present in a mole fraction of about 0.005-0.300, tyrosine can be present in a mole fraction of about 0.005-0.250, and lysine can be present in a mole fraction of about 0.3-0.7. The average molecular weight is between 2,000-40,000 Da, and preferably between about 3,000-35,000 Da. In a more preferred embodiment, the average molecular weight is about 5,000-25,000 Da. It is possible to substitute aspartic acid for glutamic acid, arginine for lysine, and/or tryptophan for tyrosine.

In another embodiment the terpolymers for use in the present invention contain lysine, glutamic acid, and alanine, hereinafter designated KEA. The average molar fraction of the amino acids in these polypeptides can also vary. For example, glutamic acid can be present in a mole fraction of about 0.005-0.300, alanine can be present in a mole fraction of about 0.005-0.600, lysine can be present in a mole fraction of about 0.2-0.7. The average molecular weight is between 2,000-40,000 Da, and preferably between about 3,000-35,000 Da. In a more preferred embodiment, the average molecular weight is about 5,000-25,000 Da. It is possible to substitute aspartic acid for glutamic acid, glycine for alanine, and/or arginine for lysine.

In another embodiment, the terpolymers for use in the present invention contain tyrosine, glutamic acid, and alanine, hereinafter designated YEA. The average molar fraction of the amino acids in these polypeptides can vary. For example, tyrosine can be present in a mole fraction of about 0.005-0.250, glutamic acid can be present in a mole fraction of about 0.005-0.300, and alanine can be present in a mole fraction of about 0.005-0.800. The average molecular weight is between 2,000-40,000 Da, and preferably between about 3,000-35,000 Da. In a more preferred embodiment, the average molecular weight is about 5,000-25,000 Da. It is possible to substitute tryptophan for tyrosine, aspartic acid for glutamic acid, and/or glycine for alamine.

In a more preferred embodiment, the mole fraction of amino acids of the terpolymers is about what is preferred for Copolymer 1. The mole fraction of amino acids in Copolymer 1 is glutamic acid about 0.14, alanine about 0.43, tyrosine about 0.10, and lysine about 0.34. The most preferred average molecular weight for Copolymer 1 is between about 5,000-9,000 Da. The activity of Copolymer 1 for the vaccine disclosed herein is expected to remain if one or more of the following substitutions is made: aspartic acid for glutamic acid, glycine for alanine, arginine for lysine, and tryptophan for tyrosine.

The molar ratios of the monomers of the more preferred terpolymer of glutamic acid, alamine, and tyrosine, or YEA, is about 0.21 to about 0.65 to about 0.14.

The molar ratios of the monomers of the more preferred terpolymer of glutamic acid, alanine and lysine, or KEA, is about 0.15 to about 0.48 to about 0.36.

The molar ratios of the monomers of the more preferred terpolymer of glutamic acid, tyrosine, and lysine, or YEK, is about 0.26 to about 0.16 to about 0.58.

The molar ratios of the monomers of the more preferred terpolymer of tyrosine, alanine and lysine, or YAK, is about 0.10 to about 0.54 to about 0.35.

The terpolymers can be made by any procedure available to one of skill in the art. For example, the terpolymers can be made under condensation conditions using the desired molar ratio of amino acids in solution, or by solid phase synthetic procedures. Condensation conditions include the proper temperature, pH, and solvent conditions for condensing the carboxyl group of one amino acid with the amino group of another amino acid to form a peptide bond. Condensing agents, for example dicyclohexyl-carbodiimide, can be used to facilitate the formation of the peptide bond. Blocking groups can be used to protect functional groups, such as the side chain moieties and some of the amino or carboxyl groups against undesired side reactions.

For example, the process disclosed in U.S. Pat. No. 3,849,650, can be used wherein the N-carboxyanhydrides of tyrosine, alanine, γ-benzyl glutamate and N ε-trifluoroacetyl-lysine are polymerized at ambient temperatures in anhydrous dioxane with diethylamine as an initiator. The γ-carboxyl group of the glutamic acid can be deblocked by hydrogen bromide in glacial acetic acid. The trifluoroacetyl groups are removed from lysine by 1 molar piperidine. One of skill in the art readily understands that the process can be adjusted to make peptides and polypeptides containing the desired amino acids, that is, three of the four amino acids in Copolymer 1, by selectively eliminating the reactions that relate to any one of glutamic acid, alanine, tyrosine, or lysine. For purposes of this application, the terms "ambient temperature" and "room temperature" mean a temperature ranging from about 20 to about 26° C.

The molecular weight of the terpolymers can be adjusted during polypeptide synthesis or after the terpolymers have been made. To adjust the molecular weight during polypeptide synthesis, the synthetic conditions or the amounts of amino acids are adjusted so that synthesis stops when the polypeptide reaches the approximate length which is desired. After synthesis, polypeptides with the desired molecular weight can be obtained by any available size selection procedure, such as chromatography of the polypeptides on a molecular weight sizing column or gel, and collection of the molecular weight ranges desired. The present polypeptides can also be partially hydrolyzed to remove high molecular weight species, for example, by acid or enzymatic hydrolysis, and then purified to remove the acid or enzymes.

In one embodiment, the terpolymers with a desired molecular weight may be prepared by a process which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined. The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by test reaction. The trifluoroacetyl-polypeptide with the desired molecular weight profile is then further treated with an aqueous piperidine solution to form a low toxicity polypeptide having the desired molecular weight.

In a preferred embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

As binding motifs of Cop 1 to MS-associated HLA-DR molecules are known (Fridkis-Hareli et al, 1999), polypeptides of fixed sequence can readily be prepared and tested for binding to the peptide binding groove of the HLA-DR molecules as described in the Fridkis-Hareli et al (1999) publication. Examples of such peptides are those disclosed in WO 005249, the entire contents of which being hereby incorporated herein by reference. Thirty-two of the peptides specifically disclosed in said application are reproduced in Table 1, hereinbelow. Such peptides and other similar peptides would be expected to have similar activity as Cop 1. Such peptides, and other similar peptides, are also considered to be within the definition of Cop 1-related peptides or polypeptides and their use is considered to be part of the present invention.

The definition of "Cop 1 related-polypeptide" according to the invention is meant to encompass other synthetic amino acid copolymers such as the random four-amino acid copolymers described by Fridkis-Hareli et al., 2002, as candidates for treatment of multiple sclerosis, namely copolymers (14-, 35- and 50-mers) containing the amino acids phenylalanine, glutamic acid, alanine and lysine (poly FEAK), or tyrosine, phenylanine, alanine and lysine (poly YFAK), and any other similar copolymer to be discovered that can be considered a universal antigen similar to Cop 1 and polyYE.

TABLE 1

| SEQ ID NO. | Peptide Sequence |
|---|---|
| 1 | AAAYAAAAAAKAAAA |
| 2 | AEKYAAAAAAKAAAA |
| 3 | AKEYAAAAAAKAAAA |
| 4 | AKKYAAAAAAKAAAA |
| 5 | AEAYAAAAAAKAAAA |
| 6 | KEAYAAAAAAKAAAA |
| 7 | AEEYAAAAAAKAAAA |
| 8 | AAEYAAAAAAKAAAA |
| 9 | EKAYAAAAAAKAAAA |
| 10 | AAKYEAAAAAKAAAA |
| 11 | AAKYAEAAAAKAAAA |
| 12 | EAAYAAAAAAKAAAA |
| 13 | EKKYAAAAAAKAAAA |
| 14 | EAKYAAAAAAKAAAA |
| 15 | AEKYAAAAAAAAAA |
| 16 | AKEYAAAAAAAAAA |
| 17 | AKKYEAAAAAAAAA |
| 18 | AKKYAEAAAAAAAA |
| 19 | AEAYKAAAAAAAAA |
| 20 | KEAYAAAAAAAAAA |
| 21 | AEEYKAAAAAAAAA |
| 22 | AAEYKAAAAAAAAA |
| 23 | EKAYAAAAAAAAAA |
| 24 | AAKYEAAAAAAAAA |
| 25 | AAKYAEAAAAAAAA |
| 26 | EKKYAAAAAAAAAA |
| 27 | EAKYAAAAAAAAAA |
| 28 | AEYAKAAAAAAAAA |
| 29 | AEKAYAAAAAAAAA |
| 30 | EKYAAAAAAAAAAA |
| 31 | AYKAEAAAAAAAAA |
| 32 | AKYAEAAAAAAAAA |

According to the present invention, the preferred copolymer for use in the vaccine of the invention is Copolymer 1, herein referred to also as Cop 1, most preferably in the form of its acetate salt known under the generic name Glatiramer acetate. Glatiramer acetate has been approved in several countries for the treatment of multiple sclerosis (MS) under the trade name, COPAXONE® (a trademark of Teva Pharmaceuticals Ltd., Petah Tikva, Israel). Several clinical trials demonstrated that Cop 1 is well tolerated with only minor side reactions which were mostly mild reactions at the injection site (Johnson et al, 1995).

As mentioned before, mutations in the SOD1 gene are one genetic cause for familial ALS (Rosen et al., 1993; Brown, 1995). Several mouse models that express the mutated SOD1 genes develop motor neuron degeneration similar to that in humans (Gurney et al., 1994; Ripps et al., 1995; Kong and Xu, 1998). The initial characterization of these mouse lines has proven that a dominant gain of an adverse property by the mutated enzymes causes motor neuron degeneration (for review, see Bruijn and Cleveland, 1996). In addition, these analyses confirmed numerous pathological features that have been observed in humans (Hirano, 1991; Chou, 1992). Understanding this mutation, called SOD1 alteration, yielded an accepted animal model (ALS mice) for testing therapies for familial ALS. Since SOD1-related familial ALS and sporadic ALS (which accounts for 90% of all ALS cases) have similar symptoms and pathological features, the transgenic mouse carrying a mutated SOD1 gene is an accepted animal model for testing therapies for both familial and sporadic ALS forms, and is the model used by the ALS Therapy Development Foundation (ALS-TDF). ALS mice develop a motor disease that closely resembles ALS. The motor dysfunction eventually causes their death.

According to the present invention, ALS mice which were immunized with a vaccine of Cop 1 emulsified in CFA or in an adjuvant suitable for human use were shown to be protected from motor nerve degeneration, in spite of the oxidative stress conditions created by the overexpression of SOD. Thus, vaccination with the "universal" weak self-reactive antigen Cop 1 in CFA prolonged by 52 days the life span of ALS mice (mean±SD, 263±8 days, n=14) compared to untreated matched controls (211±7 days; n=15; P<0.0001). The vaccination significantly improved motor activity in the clinical and pre-clinical stages. In addition, vaccination with Cop 1 also prevented acute motor neuron degeneration after facial nerve axotomy: almost 200% more motor neurons survived in vaccinated mice than in axotomized controls (P<0.05). These results suggest that the concept of autoimmunity as protective can be extended to include motor neuron diseases. They also have potentially dramatic clinical implications.

The adjuvants used for the immunization according to the invention are aluminum-based adjuvants. More commonly used in vaccines containing virus-derived antigens such as hepatitis B surface antigen or *Haemophilus influenza* type b capsular polysaccharide, these adjuvants are for the first time used together with synthetic copolymers, particularly with Cop 1.

The dosage of Cop 1 or PolyYE to be administered will be determined by the physician according to the age of the patient and stage of the disease and may be chosen from a range of 10-80 mg, although any other suitable dosage is encompassed by the invention. The administration may be made at least once a month or at least once every 2 or 3 months, or less frequently, but any other suitable interval between the immunizations is envisaged by the invention according to the condition of the patient.

The vaccine of the invention may be administered by any suitable mode of administration, including orally, intramuscularly, subcutaneously and intradermally, with or without adjuvant.

When administered together with Riluzole or any other drug suitable for treatment of MND, particularly ALS, the additional drug is administered at the same day of vaccination, and daily thereafter, according to the manufacturer's instructions, with no association to the vaccine regimen. For example, the daily dose of Riluzole is 100 mg.

The following examples illustrate certain features of the present invention but are not intended to limit the scope of the present invention.

EXAMPLES

Materials and Methods

Animals. Mice of the C57BL/6J strain, aged 8-13 weeks, were supplied by the Animal Breeding Center of The Weizmann Institute of Science (Rehovot, Israel). Prior to their use in the experiments, the mice were anesthetized by intraperitoneal administration of 80 mg/kg ketamine and 16 mg/kg xylazine. Transgenic mice overexpressing the defective human mutant SOD1 allele containing the Gly93→Ala (G93A) gene (B6SJL-TgN (SOD1-G93A)1Gur (herein "ALS mice") were purchased from The Jackson Laboratory (Bar Harbor, Me., USA). All animals were handled according to the regulations formulated by the Institutional Animal Care and Use Committee (IACUC).

Materials. Cop 1 (median MW: 7,200 dalton) was from Teva Pharmaceuticals Ltd. (Petah Tikva, Israel). Aluminum hydroxyphosphate gel (REHYDRAPHOS™ Vaccine Adjuvant, herein Alum-phos) was purchased from Reheis (NJ, USA). Complete Freund's adjuvant containing 0.5 mg/ml *Mycobacterium tuberculosis* (CFA) was purchased from Difco (Detroit, Mich., USA), if not stated otherwise.

Immunization. Mice were immunized with Cop 1 emulsified in CFA or in Cop 1-Alum-phos (100 µg in a total volume of 100 µl). Alum-phos was mixed vigorously with Cop 1 in a ratio of 1:4. Each vaccine was injected subcutaneously (SC) at one site in the flank of the mice. Control mice were injected with mannitol in either CFA or in Alum-phos.

Glutamate injection. The right eye of an anesthetized C57B BL/6J mouse was punctured with a 27-gauge needle in the upper part of the sclera, and a 10-µl Hamilton syringe with a 30-gauge needle was inserted as far as the vitreal body. Mice were injected with a total volume of 1 µl (200 nmol) of L-glutamate dissolved in saline.

Labeling of retinal ganglion cells (RGC) in mice. RGCs were labeled 72 hours before the end of the experiment. Mice were anesthetized and placed in a stereotactic device. The skull was exposed and kept dry and clean. The bregma was identified and marked. The designated point of injection was at a depth of 2 mm from the brain surface, 2.92 mm behind the bregma in the anteroposterior axis and 0.5 mm lateral to the midline. A window was drilled in the scalp above the designated coordinates in the right and left hemispheres. The neurotracer dye FluoroGold (5% solution in saline; Fluorochrome, Denver, Colo.) was then applied (1 µl, at a rate of 0.5 µl/min in each hemisphere) using a Hamilton syringe, and the skin over the wound was sutured. Retrograde uptake of the dye provides a marker of the living cells.

Assessment of RGC survival in mice. Mice were given a lethal dose of pentobarbitone (170 mg/kg). Their eyes were enucleated and the retinas were detached and prepared as flattened whole mounts in paraformaldehyde (4% in PBS). Labeled cells from 4-6 selected fields of identical size (0.7 mm$^2$) were counted. The selected fields were located at approximately the same distance from the optic disk (0.3 mm) to overcome the variation in RGC density as a function of distance from the optic disk. Fields were counted under the fluorescence microscope (magnification ×800) by observers blinded to the treatment received by the mouse. The average number of RGCs per field in each retina was calculated.

Amyotrophic lateral sclerosis model. Three ALS mice, aged 75 days, were vaccinated with Cop-1 emulsified in Alum-phos (100 µg Cop-1 in a total volume of 100 µl, one subcutaneous injection in the flank). The mice were given a booster injection a week later and monthly injections thereafter. Three additional transgenic mice were not immunized and served as a control for spontaneous progression of the disease. The muscle strength was evaluated by blindly testing the time of hanging of each mouse on a rotating vertical rod. Since the maximal time that most of the animals were able to hang on the rotating rod was 5 minutes, each experiment was continued up to 5 minutes.

Muscle strength test. The test was performed as previously described (Kong and Xu, 1998). Mice were allowed to grasp and hold onto a vertical wire (2 mm in diameter) with a small loop at the lower end. A vertical wire allows mice to use both fore- and hindlimbs to grab onto the wire. The wire was maintained in a vertically oriented circular motion (the circle radius was 10 cm) at 24 rpm. The time that the mouse was able to hang onto the wire was recorded with a timer. Because most mice fell within 5 min, the testing was cut off at 5 min. Mice were usually tested once a week and testing continued until they could no longer hang onto the wire.

Data analysis. Survival data were analyzed by the Mantel-Cox test or Cox's proportional hazards regression analysis. Statistical significance was tested by one-way ANOVA, followed by a post-hoc Student-Neuman-Keuls procedure with the SPSS-PC software program (SPSS, Chicago, Ill.).

Example 1

Neuronal Protection Against Glutamate Toxicity by Active Vaccination with Cop 1 Emulsified in Alum-phos It was first examined whether glutamate-induced toxicity can be blocked by active vaccination with Cop 1 emulsified in CFA or in Alum-phos. CFA is an adjuvant not approved for human use and is used frequently only in laboratory animal experiments. Alum-phos and other aluminum hydroxide-based adjuvants have received FDA and other authorities approval and are extensively used in veterinary and human vaccines.

Cop 1 emulsified either in CFA or in Alum-phos (100 μg Cop 1 in total volume of 100 μl) was injected subcutaneously at one site in the flank of C57BL/6J mice, and seven days later glutamate (200 nmol) was injected into the vitreal body of the mice. After seven days the surviving RGCs were counted. The survival of RGCs following glutamate toxicity without any prior immunization was taken as 100%.

As shown in Table 2, pre-immunization with Cop-1 either in CFA or in Alum-phos seven days before glutamate injection yielded a significant protection of retinal ganglion cells against glutamate toxicity, but the protection with Cop 1 emulsifie in Alum-phos was significantly higher than in CFA.

TABLE 2

Neuronal protection against glutamate toxicity by active vaccination with Cop-1 in CFA or in Alum-phos

| | RGC survival (% of non-immunized) | |
|---|---|---|
| | Control Immunization | Cop-1 |
| CFA | 98 ± 3%; n = 11 | 118 ± 8.2%*; n = 9 |
| Alum-phos | 108 ± 11%*; n = 8 | 135 ± 7%*; n = 8 |

*p < 0.05; 2-tailed Student's t-test.

Example 2

Neuronal Protection Against Glutamate Toxicity by Vaccination with Cop 1 or PolyYE without or with Adjuvant Glutamate toxicity is one of the risk factors in ALS neurodegeneration. To examine the efficacy of immunization with Cop 1 and PolyYE without adjuvant to protect the neurons from glutamate toxicity, the retina of C57BL mice were exposed to excess amount of glutamate. The C57BL mice were divided into 4 experimental groups:
1. Animals that were not immunized—negative control, n=9
2. Animals that were immunized with 25 μg PolyYE per mice, n=10
3. Animals that were immunized with 225 μg PolyYE per mice, n=10
4. Animals that were immunized with 75 μg Cop 1 per mice, n=7

The treated groups were immunized with PolyYE or Cop 1 dissolved in 100 μl PBS 7 days prior to intraocular glutamate injection. The number of RGCs that survived 7 days after exposure to elevated level of glutamate was counted and calculated as percentage of normal eyes. The results are shown in FIG. 1. RGC survival in all the treated groups (groups 2-4) was significantly (p<0.001 t-test) higher than the negative control group.

Figure 2A:
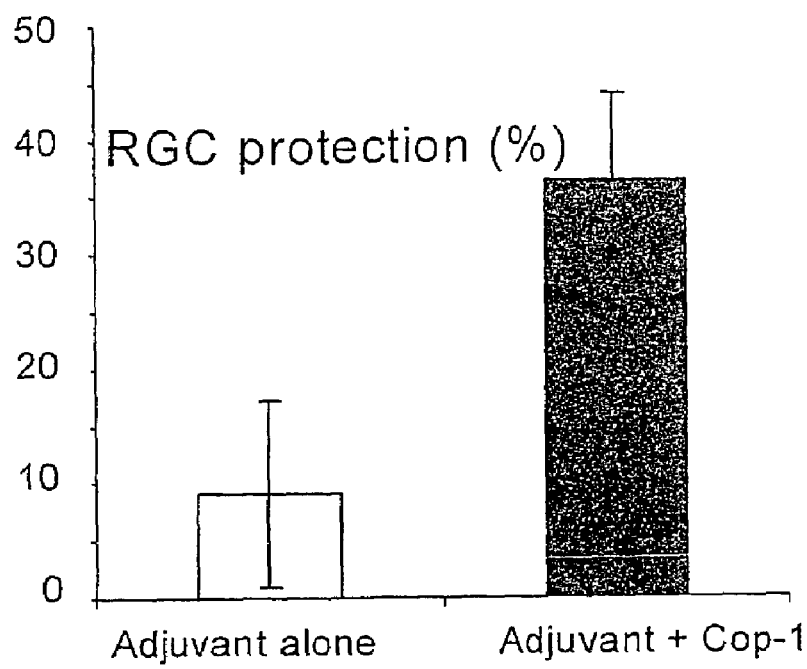
FIGS. 2A-B show that immunization with Cop 1 (2A) or PolyYE (2B) in adjuvant (CFA) protects mice RGCs from glutamate toxicity.
Figure 2B:
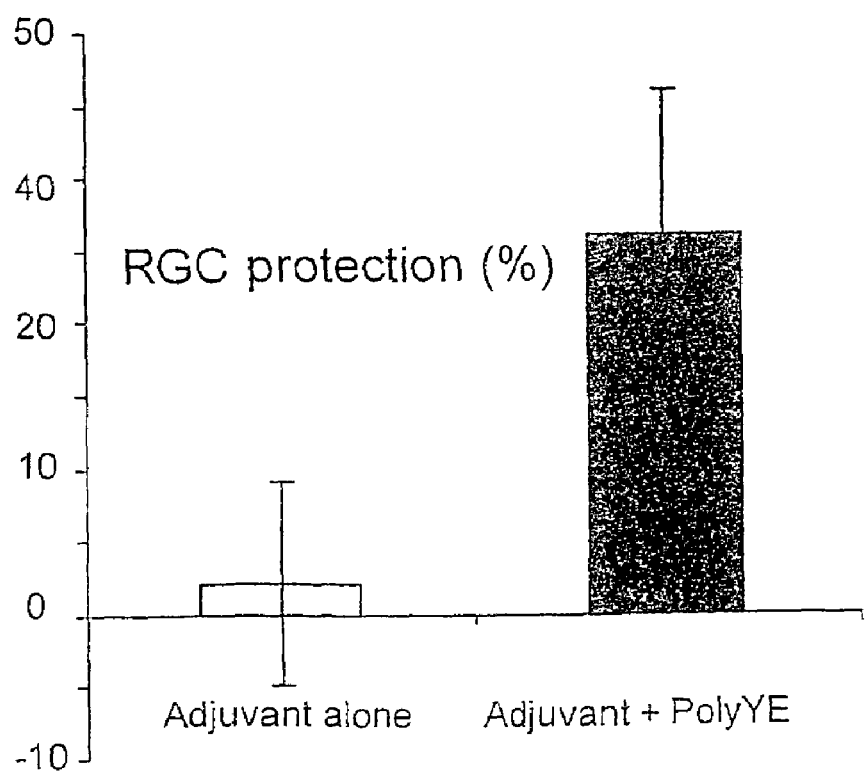

In additional experiments, C57B1 mice were treated with Cop 1 (100 μg) emulsified in Alum-phos (n=8) or with Alum-phos alone (n=8) or PolyYE (100 μg) emulsified in CFA (n=24) or with adjuvant alone (negative control) (n=27) (100 μl), 7 days prior to intraocular glutamate injection. The number of RGCs that survived 7 days after exposure to elevated level of glutamate was counted. Protection was calculated as percentage of RGC that survived out of the total RGC loss in the non-treated group. The results are shown in FIGS. 2A-B. RGC survival in the Cop 1-treated group (FIG. 2A) and the PolyYE-treated group (FIG. 2B) was significantly higher than the negative control groups that received adjuvant alone.

Cop 1 of high molecular weight sizes (median MW: 12,600, 15.500, and 22,000 dalton) are tested in the glutamate toxicity model. The efficacy in evoking specific neuroprotective response is determined in the model of acute glutamate toxicity in RGCs as described above. C57BL/6 mice (total of 5 groups per experiment, 10 animals per group) are immunized 14 days before intraocular injection of glutamate (200 nmol), and RGC survival is examined 7 days after glutamate injection. Three doses of Cop 1 of each MW is tested and compared to negative control (glutamate only) and positive control (75 μg Cop 1 of MW 7,200 d, 7 days prior to glutamate toxicity).

Example 3

Neuroprotective Effect of Vaccination with Cop 1 and Poly-YE in the Glaucoma Model Glaucoma is a chronic neurodegenerative disease with progressive loss of visual neurons that eventually leads to blindness. Increased intraocular pressure (IOP) is considered the major risk factor and believed to be the primary cause of neuronal death. Accordingly, biochemical agents or surgery designed to reduce IOP are the current standard therapy. Nevertheless, lowering IOP is not always sufficient to stop neuronal loss. Moreover, optic nerve degeneration sometimes occurs in the absence of elevated IOP, a condition called normal tension glaucoma (occurring in approximately one third of glaucoma patients). Thus, neuroprotective therapy is considered appropriate. We used a model of chronic elevation in IOP of the rat to examine the ability of Cop 1 or PolyEY vaccination to attenuate the death of neurons which are under continuous stress conditions, as it might occur in ALS patients. Since glaucoma is a chronic neurodegenerative disease as ALS, neuroprotection afforded in the glaucoma model may be indicative of a similar neuroprotection in ALS.

Induction of high IOP was performed as follows: Using a Haag-Streit slit lamp emitting blue-green argon laser irradiation, the right eye of anesthetized adult male Lewis rats were treated by 80-120 applications directed towards three of the four episcleral veins and towards 270 degrees of the limbal plexus. The laser beam was applied with a power of 1 watt for 0.2 seconds, producing a spot size of 100 mm at the episcleral veins and 50 mm at the limbal plexus. At a second laser session one week later, the same parameters were used except that the spot size was 100 mm for all 5 applications. Irradiation was directed towards all four episcleral veins and 360 degrees of the limbal plexus 24.

To measure the elevation of IOP, the rats were injected intraperitoneally with 10 mg/ml acepromazine, a sedative drug that does not reduce IOP, and 5 minutes later the pressure in both eyes was measured using a Tono-Pen XL tonometer (Automated Ophthalmics, Ellicott City, Md., USA), after applying Localin to the cornea. Average of 10 measurements taken from each eye was calculated. One week after the first laser treatment, the IOP reached levels of about 30 mmHg without any significant change until the end of the experiment (3 weeks after the first laser treatment) as shown in Table 3 below.

To determine RGC survival, the hydrophilic neurotracer dye dextran tetramethylrhodamine (Rhodamine Dextran) (Molecular Probes, Oregon, USA) was applied 3 weeks after the first laser treatment directly into the intra-orbital portion of the optic nerve. Only axons that survive the high IOP and remain functional, and whose cell bodies are still alive, can take up the dye and demonstrate labeled RGCs. The rats were killed 24 hours later and their retinas were excised, whole-mounted, and the labeled RGCs were counted under magnification of ×800 in a Zeiss fluorescent microscope. From each retina four fields were counted, all with the same diameter (0.076 mm$^2$) and at the same distance from the optic disk. RGCs were counted by an observer blinded to the identity of the retinas.

Table 3 summarizes the RGCs survival in rats with normal IOP and in rats with a laser-induced increase in IOP 3 weeks later.

TABLE 3

| | 3 weeks post laser | | |
|---|---|---|---|
| Normal Mean RGCs ± SD (per mm$^2$) | Mean IOP ± SD | Mean RGCs ± SD (per mm$^2$) | % Survival |
| 2525 ± 372 (n = 5) | 29.92 ± 2.38 (n = 10) | 1420 ± 272 | 53.9 |

3a. Effect of PolyEY Vaccination on RGC Survival in the Glaucoma IOP Model

Figure 3A:
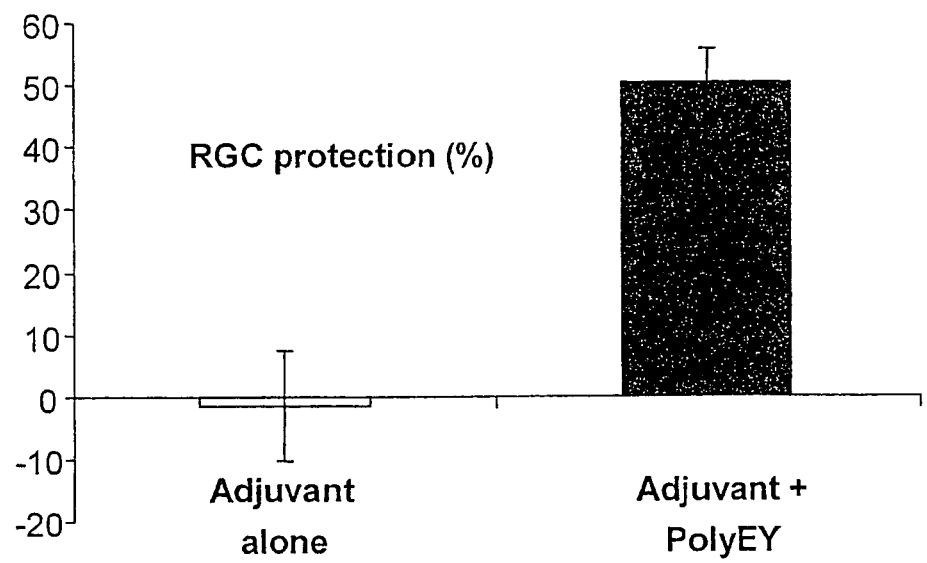
FIGS. 3A-B show the effect of immunization with PolyYE (FIG. 3A) or Cop 1 (FIG. 3B) on RGC survival in the glaucoma intraocular pressure (IOP) model.

SPD rats were immunized with PolyEY (500 μg) emulsified with CFA one hour after the first laser treatment (n=9). One control group was immunized with CFA without the antigen (n=7) and the second control group was injected with PBS alone (n=5). As shown in FIG. 3A, though the IOP remained elevated throughout the experimental period, PolyEY-, but not PBS-immunized rats, showed significant increased survival of their RGCs compared to non-immunized rats. Protection of RGC was calculated as percentage of cells survived in the treated groups out of the total cell loss in the non-immunized group.

3b. Effect of Cop 1 Vaccination RGC Survival in the Glaucoma IOP Model

Figure 3B:
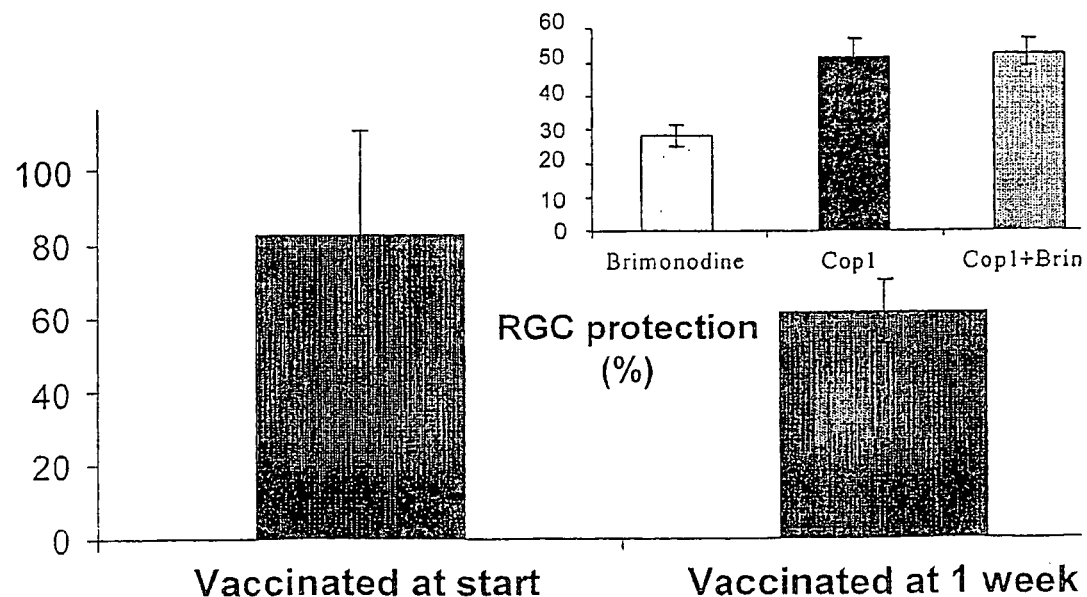

Using the rat model of IOP-elevation, Cop 1 was shown to attenuate neuronal loss when given (500 μg in CFA) at the start of IOP elevation or a week later (see FIG. 3B), despite the fact that the IOP remained high and nerve degeneration has already started. Additionally, Cop 1 vaccination, given together with the IOP-lowering drug brimonodine resulted in greater RGC protection than using brimonodine alone (see FIG. 3B, insert).

Example 4

Cop 1 Immunization Protects Motor Nerve Degeneration in Transgenic Mutant SOD1 Mice (ALS Mice)

To test whether Cop 1 immunization can protect from the progression of motor neuron degeneration, ALS mice SOD1 (n=3) were immunized with Cop 1 in Alum-phos when they were 75 days old and a boost was administered one week later. Then they were immunized every 30 days. A control group (n=3) of ALS mice was not immunized with Cop 1. The mice were then tested several times per week for muscle strength, by blindly testing the time of hanging on a rotating vertical rod. Each experiment lasted 5 min.

Figure 4A:
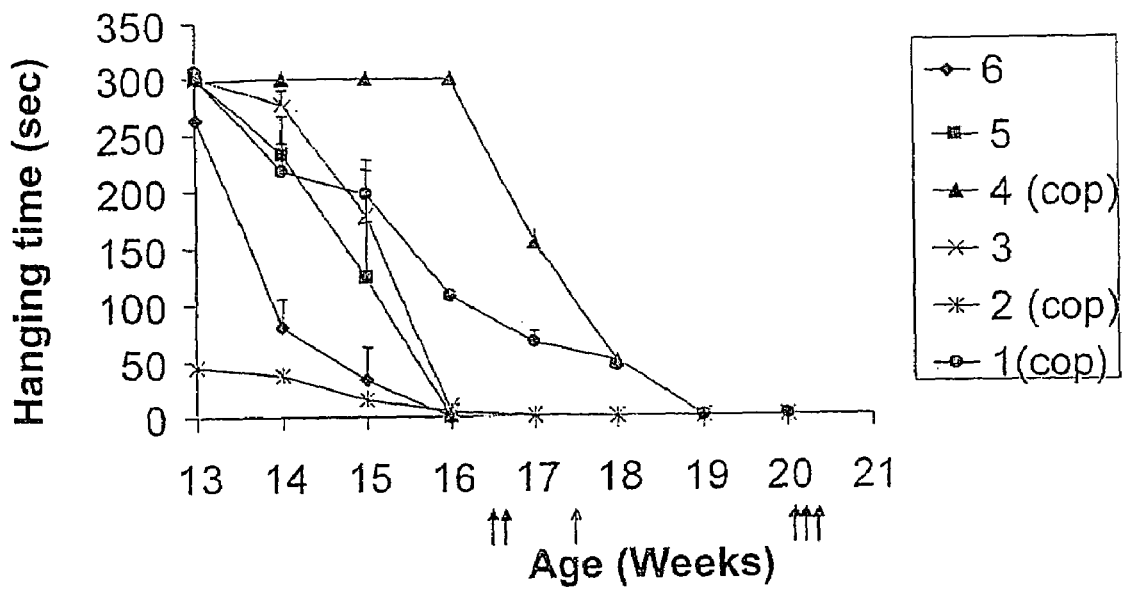
FIGS. 4A-4B depict results of muscle strength test carried out with transgenic mice overexpressing human mutant SOD1 (hereinafter "ALS mice").
Figure 4B:
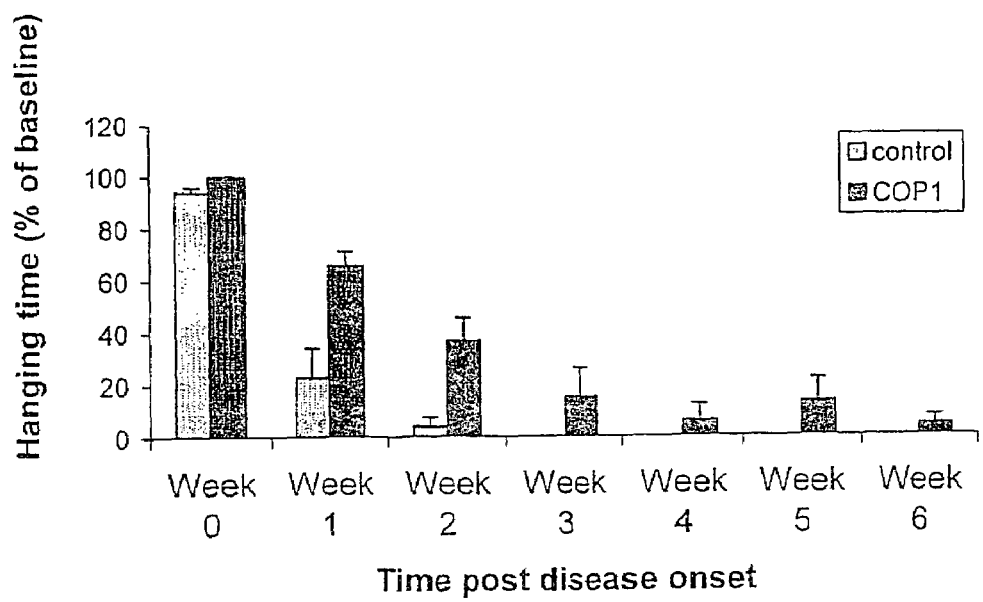

The development of muscle weakness in the mice is depicted in FIGS. 4A-B. FIG. 4A depicts the average hanging time for each animal per week (results are the mean±SEM. As shown, two of the Cop 1-immunized animals (mice 1 and 4) exhibited longer hanging time than the non-immunized mice.

The onset of the decline in muscle strength varied among individual mice. To assess the effect of the vaccination on the rate of decline in each mouse, the muscle strength at any given time was compared to that found one week before the decline began.

FIG. 4B shows the synchronized plot of muscle strength decline in individual transgenic mice. It is clear that mice immunized with Cop-1 (black columns) showed a significantly lower rate of muscle strength decline, regardless of their strength on the day of immunization. Thus, they retained motor power for a longer period of time as compared to non-immunized animals.

Figure 5:
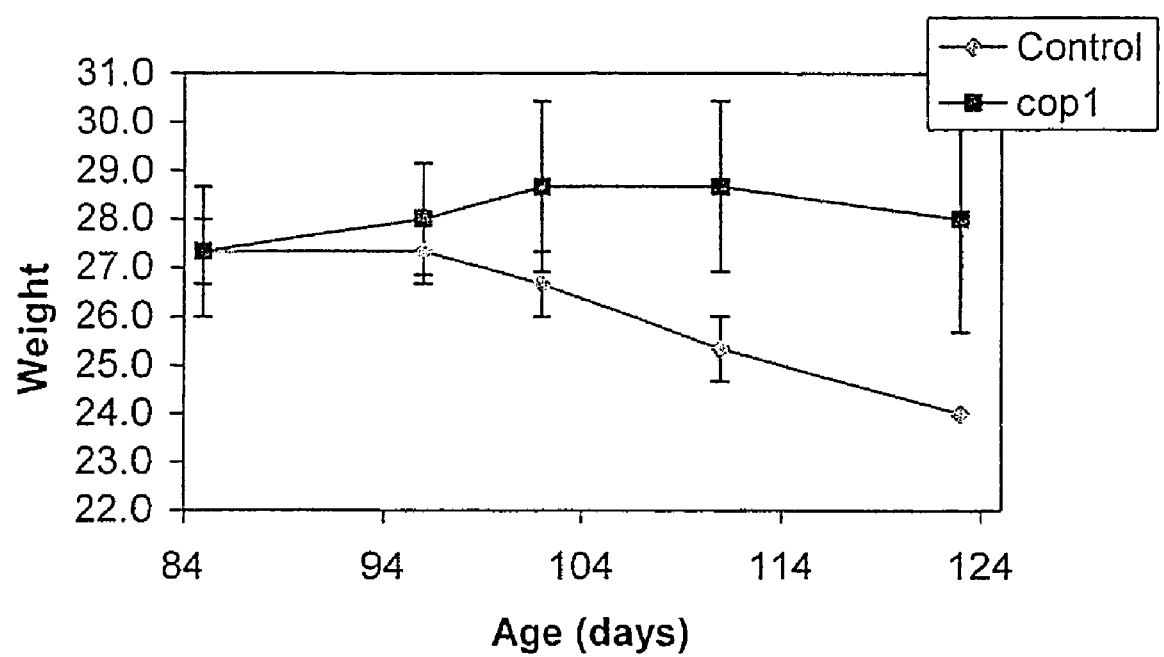
FIG. 5 shows the preservation of body weight in ALS mice immunized with Cop 1 in Alum-phos (black squares) as compared to non-immunized mice (gray diamonds).

The beneficial effect of Cop1 immunization is also reflected in the mice body weight. As shown in FIG. 5, as the disease progressed, the Cop-1 immunized transgenic mice also showed a slower loss of body weight. Between the age of 86 to 111 days all non-immunized transgenic mice lost 2 grams of their body weight. In contrast, in the Cop 1-immunized group, one mouse had no change and two gained 2 grams to their body weight.

The immunization with Cop 1 also affected the mortality rate of the transgenic mice. With progression of the disease, the mice became paralyzed and died. Immunization with Cop 1 significantly prolonged the life of the transgenic mice: whereas the untreated mice died 2, 3 and 4 weeks after onset of the disease, one Cop 1-immunized mice survived for 4 weeks and the other two for 7 weeks after onset of the disease (Table 4). At the time of death, the Cop 1-immunized transgenic mice were 3 weeks older, on average, than the non-immunized mice.

TABLE 4

Cop 1 immunization prolongates life span of transgenic mice overexpressing mutant human SOD-1.

| | Age of death (weeks) | Death after disease onset (weeks) |
|---|---|---|
| Control | 16.3 ± 0.3 (n = 3) | 3 ± 0.6 (n = 3) |
| Cop 1 | 20 ± 0 (n = 3) | 6 ± 1 (n = 3) |

Example 5

Cop-1 Treatment Increases the Life Expectancy of ALS Mice

Figure 6:
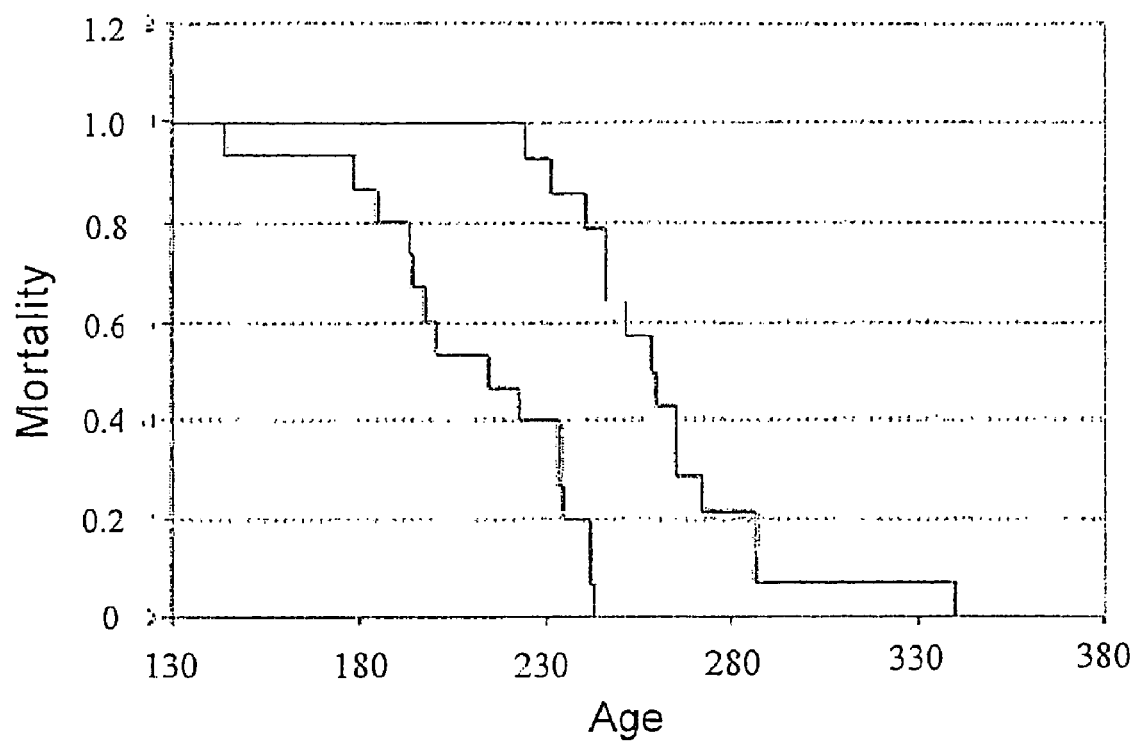
FIG. 6 is a graph showing life expectancy in ALS mice immunized with Cop-1 in CFA. Paralysis is caused by the progressive loss of motor neurons from the spinal cord. Non-vaccinated controls (n=15) became paralyzed in one or more limbs and died by the age of 211±7 days (mean±SD). Cop 1-treated mice survived for 263±8 days.

Fourteen ALS mice, aged 60 days, were vaccinated with Cop 1 (75 μg) emulsified in CFA (Difco Laboratories, Heidelberg, Germany) containing 5 mg/ml *Mycobacterium tuberculosis*. The emulsion (total volume 200 μl) was injected into the hind foot pad, and the mice were subsequently treated daily with oral Cop 1 (12.5 mg/kg/day) given in the drinking water. Mice immunized at the age of 60 days with Cop-1 and untreated control mice were observed daily and weighed weekly. Their motor activity and mortality were monitored. The age at symptom onset was determined as the age (in days) at the time of first appearance of tremors and/or shaking of the limbs, or hanging (rather than splaying out) of the hind limbs when the mouse was held in the air by the tail. Loss of the righting reflex was taken to indicate the end stage of the disease. Paralysis is caused by the progressive loss of motor neurons from the spinal cord. As shown in FIG. 6, non-vaccinated controls (n=14) became paralyzed in one or more limbs and died by the age of 211±7 days (mean±SD). Cop-1-treated mice survived for 263±8 days. Thus, vaccination with Cop-1 dramatically increased the life expectancy of the ALS mice (FIG. 6).

Figure 7:
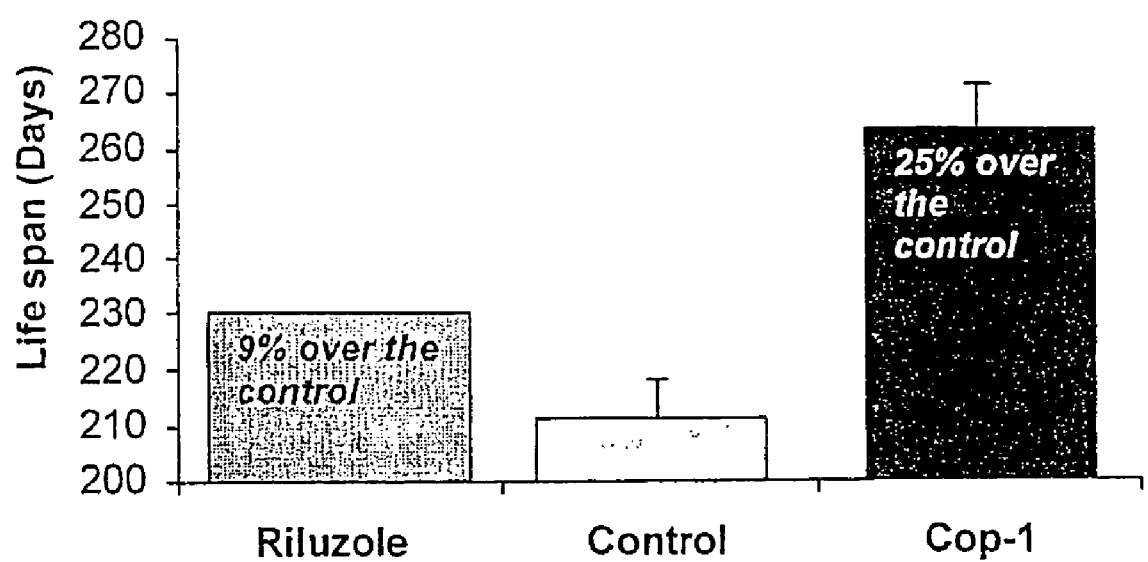
FIG. 7 shows life expectancy in ALS mice immunized with Cop-1 in CFA and ALS mice-treated with Riluzole. Riluzole-treated and Cop 1-immunized ALS mice showed an increase of 9% and 25%, respectively, over the non-vaccinated control mice.

As a positive control, 15 ALS mice were given a daily dose (30 mg/kg) of Riluzole, the only drug currently given to ALS patients. As shown in FIG. 7, the Riluzole-treated mice showed an increase of 9% in survival over the control, while the Cop 1-treated mice showed an increase of 25% over the control.

Figure 8:
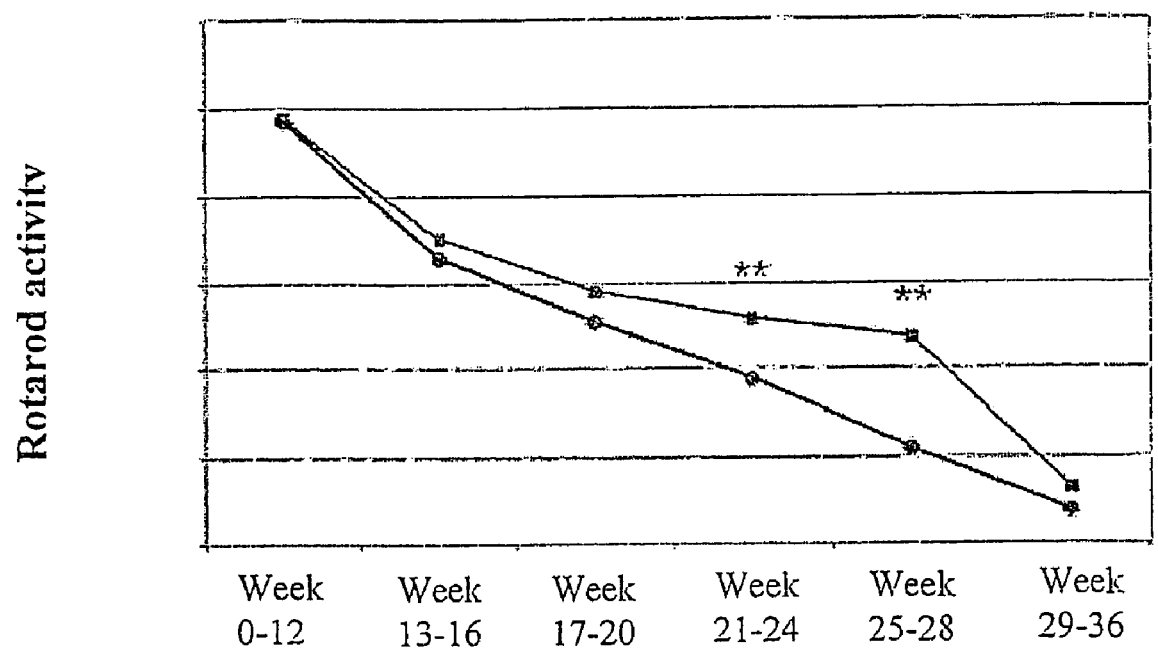
FIG. 8 shows average rotatory activity measured at the indicated time points in Cop 1-treated and untreated ALS mice. The mice were allowed to grasp and hold onto a vertical wire (2 mm diameter) with a small loop at the lower end. Their activity was recorded individually by a computerized system and assessed daily. For statistical evaluation, the rotarod activity was normalized to the mean activity of each mouse from day 40 to day 60. Data are expressed as the mean±standard error of the mean (SEM). Significant differences between treated and untreated mice were observed at the following time periods: between days 12 and 20 ($P<0.058$), between days 21 and 24 ($P<0.0079$), and between days 25 and 28 ($P<0.0017$).

In addition to the increase of almost 25% in life span, disease onset (manifested by motor performance) was delayed, indicating that the benefit was also expressed in the quality of life, both at pre-clinical and at clinical stages (FIG. 8). The mice were allowed to grasp and hold onto a vertical wire (2 mm diameter) with a small loop at the lower end. Normal values for each mouse were obtained by assessing nightly motor activity (from 8 PM to 8 AM) between the ages of 40 and 60 days, using the rotarod apparatus (LMTB, Berlin). Their activity was recorded individually by a computerized system and assessed daily. For statistical evaluation, the rotarod activity was normalized to the mean activity of each mouse from day 40 to day 60. Data are expressed as the mean±standard error of the mean (SEM). Rotarod testing and weight were compared by analysis of variance (ANOVA). Statistical significance was tested by one-way ANOVA followed by a post-hoc Student-Neuman-Keuls procedure with the SPSS-PC software program (SPSS, Chicago, Ill.). Significant differences between Cop-1-treated and untreated mice were observed at the following time periods: between days 12 and 20 ($P<0.058$), between days 21 and 24 ($P<0.0079$), and between days 25 and 28 ($P<0.0017$).

Example 6

Treatment of ALS Mice with Cop 1 without Adjuvant

ALS mice (15 animals per group) were divided into 11 experimental groups:

1. Non-treated mice—negative control group.
2. Riluzole-treated mice—30 mg/kg/day
3. Mice immunized with Cop 1/CFA —75 μg primary vaccination followed by daily oral administration of Cop 1 (12.5 mg/kg_—positive control group.
4. Mice immunized with two injections of 75 μg Cop 1: the first one on day 45 and the second one on day 59.
5. Mice immunized as in group #4, followed by a single injection of 100 μg Cop 1 on day 87.
6. Mice immunized with two injections of 150 μg Cop 1: the first one on day 45 and the second one on day 59.
7. Mice immunized with two injections of 75 μg Cop 1: the first one on day 83 and the second one on day 97.
8. The same as group #4, with Riluzole 30 mg/kg/day.
9. The same as group #5, with Riluzole 30 mg/kg/day
10. The same as group #6, with Riluzole 30 mg/kg/day.
11. The same as group #7, with Riluzole 30 mg/kg/day.

The motor activity and body weight of the mice are monitored once a week, stating two weeks before beginning of treatment. The end stage criterion for sacrifice of the animals is defined by their inability to right themselves within 30 seconds when placed on either side on a flat surface. The decision is made by an independent veterinarian as requested by the animal protocol.

Example 7

Cop-1 Administration Protects Against Motor Neuron Degeneration after Facial Nerve Axotomy Transection of the facial nerve in the adult mouse is known to cause an easily visible late degeneration of 20% to 35° 1% of the axotomized motor neurons. Therefore, axotomy of the facial nerve provides a model for ALS, which is a disease characterized by progressive motoneuron loss. The effect of immunization on the survival and function of the neurons in the facial nerve axotomy model is indicative for the potential of the treatment in attenuating neuronal loss in ALS patients.

Thirty-four adult female mice (12 weeks old, 20-25 g) of the C57BL/6JO1aHsd strain (Harlan Winkelmann, Borchen, Germany) participated in this experiment. Control animals were subjected to unilateral facial nerve axotomy and were either untreated or injected with PBS emulsified in CFA. Mice in the experimental group (n=10) were immunized with Cop 1 (total of 100 μg) or injected with PBS (n=9), both emulsified in CFA, and 7 days later were subjected to facial nerve axotomy. Mice in a third group (n=8) were axotomized without prior immunization, and mice in a fourth group (n=7) were left intact.

Seven days later a facial-facial anastomosis (FFA) was created in anesthetized mice (100 mg Ketanest® plus 5 mg Rompun® per kg body weight) by microsurgical reconnection of the proximal stump to the distal stump with two 11-0 epineural sutures (Ethicon EH 7438G, Norderstedt, Germany). The wound was closed with three 4-0 skin sutures. For assessment of recovery, facial motor neurons supplying the whiskerpad muscles were retrogradely labeled by injection of 30 μl of 1% aqueous solution of the fluorescent retrograde tracer FluoroGold plus 2% dimethylsulfoxide (DMSO) injected into the muscles of each whisker pad. Seven days later, the mice were re-anesthetized and perfused transcardially with 0.9% NaCl followed by fixation with 4% paraformaldehyde in 0.1 M phosphate buffer pH 7.4 for 20 min. The brains were removed and 50-μm-thick coronal sections were cut through the brain stems with a vibratome. Sections were observed with a Zeiss Axioskop 50 epifluorescence microscope through a custom-made HQ-Schmalband-filter set for FluoroGold (AHF Analysentechnik, Tubingen, Germany).

Eight weeks after axotomy, as shown in FIGS. 9A-D and Table 5, the mean number of FluoroGold-labeled motor neurons in the mice vaccinated with Cop-1 was significantly larger than the number obtained in the group injected with PBS in CFA or in the untreated control group (P<0.05). Treatment with Cop 1 had no effect on the number of motor neurons in the unlesioned facial nucleus. Control immunization with PBS in CFA had no protective effect.

Figure 9A:
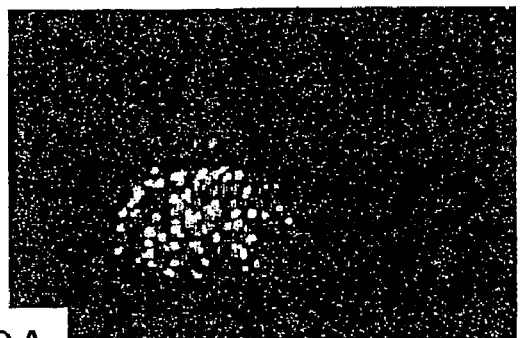
FIGS. 9A-D shows rescue of motor neurons by Cop 1 administered to mice after facial nerve axotomy. Eight weeks after axotomy the number of FluoroGold-labeled motor neurons in the brain stems of mice vaccinated with Cop-1 (FIG. 9D) was significantly larger than the number obtained in the group injected with PBS in CFA (FIG. 9B). Treatment with Cop-1 had no effect on the number of motor neurons in the unlesioned facial nucleus (FIGS. 9A, 9C). Control immunization with PBS in CFA had no protective effect.
Figure 9B:
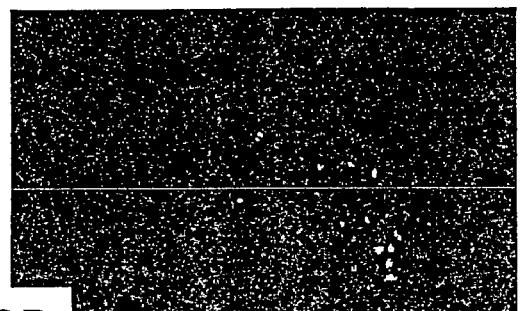
Figure 9C:
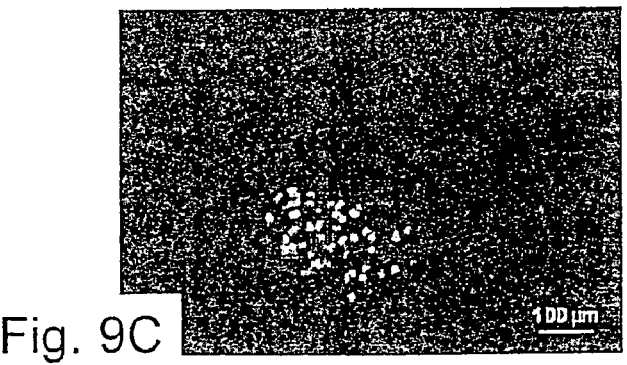
Figure 9D:
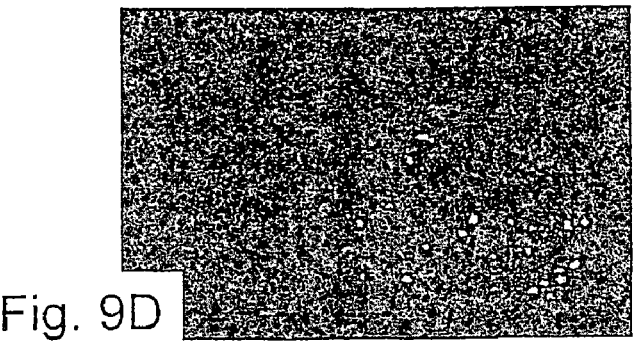

Retrograde neuronal labeling after injection of FluoroGold into the whiskerpad showed no differences in the localization or amount of motor neurons in the intact facial nucleus between mice immunized with Cop-1 in CFA (FIG. 9A) and mice injected with PBS in CFA (FIG. 9C). In contrast, the lesioned facial nucleus, after pre-treatment of mice with Cop 1 in CFA (FIG. 9B), contained significantly more labeled motor neurons than that of the lesioned facial nucleus in control animals pre-treated with PBS in CFA (FIG. 9D). Data are presented as means±standard deviation (SD). Differences between the different experimental groups were detected by applying a one-way analysis of variance (ANOVA) and a post-hoc t test for unpaired data with Bonferroni-Holm correction. P values of less than 0.05 were considered statistically significant.

Example 8

Cop-1 Administration Preserves Motor Neuron Activity after Acute Axotomy

To determine whether the larger number of motor neurons found in the Cop-1-treated axotomized mice than in the controls was associated with functional improvement, whisking behavior was biometrically analyzed. Baseline parameters of whisking behavior were documented in intact control mice. Under normal physiological conditions, the mystacial vibrissae are erect with anterior orientation. Their simultaneous sweeps, known as "whisking" or "sniffing", occur 5-11 times per second. The key movements of this motor activity are the protraction and retraction of the vibrissal hairs by the piloerector muscles, which are innervated by the buccal branch of the facial nerve. When the facial nerve is transected, the vibrissae acquire a caudal orientation and remain motionless.

Using this model, the following parameters were evaluated: (i) protraction (forward movement of the vibrissae), measured by the rostrally opened angle between the midsagittal plane and the hair shaft (large protractions are represented by small angle values); (ii) whisking frequency, represented by cycles of protraction and retraction (passive backward movement) per second; (iii) amplitude—the difference, in degrees, between maximal retraction and maximal protraction; (iv) angular velocity during protraction, in degrees per second; and (v) angular acceleration during protraction, in degrees per second.

Mice subjected to facial nerve axotomy and Cop-1 vaccination demonstrated significantly better whisking activity than the other groups of mice. This was best demonstrated by the amplitude, the angular velocity during protraction, and the angular acceleration during protraction (Table 6).

TABLE 5

Effect of Cop-1 vaccination on survival of motor neurons.

| Group | Unlesioned facial nucleus | Lesioned facial nucleus |
|---|---|---|
| A: Intact mice (n = 7) | 1559 ± 135 | 1707 ± 90*[B,C,D] |
| B: FFA only (n = 8) | 1434 ± 106 | 670 ± 178*[A,D] |
| C: FFA after PBS/CFA injection (n = 9) | 1605 ± 142 | 766 ± 104*[A,D] |
| D: FFA after vaccination with Cop-1 in CFA (n = 10) | 1640 ± 186 | 1172 ± 152*[A,B,C] |

Numerical values of the results shown in FIG. 9. Numbers (means±SD) of facial perikarya retrogradely labeled by injection of 1% FluoroGold (30 µl) in intact mice (group A) and in mice that underwent FFA only (group B), FFA after injection of PBS in CFA (group C), and FFA after vaccination with Cop 1 in CFA (group D). Superscript letters indicate the groups with significantly different values (*P<0.05). For image analysis, a CCD video camera system (Optronics Engineering Model DEI-470, Goleta, Calif.) combined with the image analyzing software Optimas 6.5 (Optimas, Bothell, Wash.) was used to manually count the retrogradely labeled facial motor neurons on the computer screen (42). Employing the fractionator principle (43), all retrogradely labeled motor neurons with visible cell nuclei were counted in every second section of the 50-µm-thick sections through the facial nucleus on both the operated and the unoperated side. Counting was done by two observers who were blinded to the treatment received by the rats.

TABLE 6

Effect of Cop-1 vaccination on recovery of whisking behavior after facial nerve axotomy

| Group | Frequency (Hz) | Angle at maximal protraction (degrees) | Amplitude (degrees) | Angular velocity during protraction (degrees/s) | Angular acceleration during protraction (degrees/s$^2$) |
|---|---|---|---|---|---|
| A: Intact mice (n = 7) | 6.0 ± 1.0 | 65.1° ± 22 | 40° ± 14*[B,C] | 627° ± 346*[B,C,D] | 20084° ± 1508*[B,C,D] |
| B: FFA only (n = 8) | 5.0 ± 2.0 | 81.2° ± 27 | 11.0° ± 6.0*[A,D] | 75° ± 43*[A] | 1655° ± 1146*[A] |
| C: FFA after injection of PBS in CFA (n = 9) | 5.3 ± 1.2 | 64.4° ± 6.3 | 22.1° ± 9.9*[A,D] | 214° ± 70*[A] | 3874° ± 889*[A] |

TABLE 6-continued

Effect of Cop-1 vaccination on recovery of whisking behavior after facial nerve axotomy

| Group | Frequency (Hz) | Angle at maximal protraction (degrees) | Amplitude (degrees) | Angular velocity during protraction (degrees/s) | Angular acceleration during protraction (degrees/s$^2$) |
|---|---|---|---|---|---|
| D: FFA after treatment with Cop-1 in CFA (n = 10) | 5.5 ± 0.9 | 68.2° ± 23.05 | 38.9° ± 10.6*$^{B,C}$ | 347.8° ± 87.3*$^A$ | 6713° ± 2071*$^A$ |

Biometrics of normal and recovering whisking behaviour in intact mice (group A) and in mice subjected to FFA only (group B), mice subjected to FFA after injection of PBS in CFA (group C), and mice subjected to FFA after injection of Cop-1 in CFA (Group D). Values are means ± SD. Superscript letters indicate groups with significantly different values (*P < .05). The two large hairs of the C-row on each side of the face were used for biometric analysis. With the mice under light ether narcosis, all other vibrissae were clipped with small fine scissors. A digital camcorder (Panasonic NV DX-110 EG) was used to videotape the actively exploring mice for 3-5 min. Following calibration, video images of whisking behavior were sampled at 50 Hz (50 fields per sec), with the video camera shutter opened for 4 msec. Images were recorded on AY-DVM 60 EK minicassettes. The video sequences were slowly reviewed and 1.5-sec sequence fragments from each mouse were selected for analysis of whisking biometrics. The selection criteria used were stable position of the head, frequency of whisking, and degree of vibrissal protraction. The selected sequences were captured by a 2D/Manual Advanced Video System PEAK Motus 2000 (PEAK Performance Technologies, Englewood, CO). The spatial model consisted of three reference points (tip of the nose and the inner angles of both eyes). Each vibrissa is represented in the spatial model by two points: its base and a point on the shaft 0.5 cm from the base.

REFERENCES

Brown R. H. (1995) "Amyotrophic lateral sclerosis: recent insights from genetics and transgenic mice" Cell 80: 687-692

Bruijn L. I., Cleveland D. W. (1996) "Mechanisms of selective motor neuron death in ALS: insights from transgenic mouse models of motor neuron disease" Neuropathol Appl Neurobiol 22:373-387

Chou S. M. (1992) "Pathology-light microscopy of amyotropic lateral sclerosis". In: Handbook of Amyotrophic Lateral Sclerosis (Smith R. A., ed.), pp. 133-181. New York: Marcel Dekker Fridkis-Hareli et al. (1999) "Binding motifs of copolymer 1 to multiple sclerosis- and rheumatoid arthritis-associated HLA-DR molecules" J. Immunol. 162 (8):4697-4704

Fridkis-Hareli et al. (2002) "Novel synthetic amino acid copolymers that inhibit autoantigen-specific T cell responses and suppress experimental autoimmune encephalomyelitis" J Clin Invest 109 (12):1635-1643

Gurney M. E. et al. (1994) "Motor neuron degeneration in mice that express a human Cu$_1$Zn superoxide dismutase" Science 264: 1772-1775

Hadano et al. (2001) "A gene encoding a putative GTPase regulator is mutated in familial amyotrophic lateral sclerosis 2" Nature Genetics 29: 166-73

Hauben et al. (2000) "Autoimmune T cells as potential neuroprotective therapy for spinal cord injury" Lancet 355: 286-287

Hirano A. (1991) "Cytopathology of amyotrophic lateral sclerosis" Adv Neurol 56:91-101

Johnson et al. (1995) "Copolymer 1 reduces relapse rate and improves disability in relapsing-remitting multiple sclerosis: results of a phase III multicenter, double-blind placebo-controlled trial. The Copolymer 1 Multiple Sclerosis Study Group," Neurology 1:65

Julien J. P. (2001) "Amyotrophic lateral sclerosis: unfolding the toxicity of the misfolded". Cell 104:581-591

Kipnis et al. (2001) "Neuronal survival after CNS insult is determined by a genetically encoded autoimmune response". J. Neurosci. 21 (13):4564-71

Kong, J. and Xu, Z. (1998) "Massive mitochondrial degeneration in motor neurons triggers the onset of amyotrophic lateral sclerosis in mice expressing a mutant SOD1" J. Neuroscience 18: 3241-3250

Moalem G. et al. (1999) "Autoimmune T cells protect neurons from secondary degeneration after central nervous system axotomy", Nature Medicine 5:49-55

Mulder D. W. et al. (1986) "Familial adult motor neuron disease: amyotrophic lateral sclerosis" Neurology 36:511-517

Munsat T. L. et al. (1989) "Adult motor neuron disease". In: Merritt's Textbook of Neurology (Rowland L. P., ed.), pp 682-687. Philadelphia: Lea & Febiger Pitt et al. (2000) "Glutamate excitotoxicity in a model of multiple sclerosis" Nature Medicine 6:67-70

Ripps M. E. et al. (1995) "Transgenic mice expressing an altered murine superoxide dismutase gene provide an animal model of amyotrophic lateral sclerosis" Proc Natl Acad Sci, USA 92: 689-693

Rosen D. R. et al. (1993) "Mutations in Cu$_1$Zn superoxide dismutaso gene are associated with familial amyotrophic lateral sclerosis" Nature 362:59-62

Rothstein J. D., et al. (1992) "Decreased glutamate transporter by the brain and spinal cord in amyotrophic lateral sclerosis". N. Eng. J. Med; 326: 1464-68

Turner et al. (2001) "Clinical trials in ALS: An overview. Seminars in Neurology" 21: 167-175

Yang et al. (2001) "The gene encoding alsin, a protein with three guanine-nucleotide exchange factor domains, is mutated in a form of recessive amyotrophic lateral sclerosis", Nature Genetics 29: 160-165

The invention claimed is:

1. A method for protection against motor nerve degeneration, and/or protection from glutamate toxicity in a patient suffering from amyotrophic lateral sclerosis (ALS), which comprises immunizing said patient with a vaccine comprising a therapeutically effective amount of an active agent selected from the group consisting of Copolymer 1, a Copolymer 1-related peptide, and a Copolymer 1-related polypeptide.

2. The method according to claim 1, wherein said vaccine comprises the active agent without an adjuvant.

3. The method according to claim 1, wherein said vaccine comprises the active agent emulsified in an adjuvant suitable for human clinical use.

4. The method according to claim 3, wherein said adjuvant is selected from the group consisting of aluminum hydroxide, aluminum hydroxide gel, and aluminum hydroxyphosphate.

5. The method according to claim 4, wherein said adjuvant is amorphous aluminum hydroxyphosphate having an acidic isoelectric point and an aluminum to phosphorus ratio of 1:1.

6. The method according to claim 1, wherein said active agent is Copolymer 1.

7. The method according to claim 1, wherein said active agent is a Copolymer 1-related peptide or a Copolymer 1-related polypeptide.

8. The method according to claim 1, wherein said vaccine is administered at least once a month.

9. The method according to claim 1, wherein said vaccine is administered at least once every 2-3 months.

10. The method according to claim 1, further including administering a drug, other than Copolymer 1, a Copolymer 1-related peptide or a Copolymer 1-related polypeptide, suitable for treatment of ALS.

11. The method according to claim 10, wherein said drug suitable for treatment of ALS is Riluzole.

* * * * *

SEQUENCE LISTING

<160> NUMBER OF SEQ ID NOS: 32

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Ala Ala Ala Tyr Ala Ala Ala Ala Ala Lys Ala Ala Ala Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2

Ala Glu Lys Tyr Ala Ala Ala Ala Ala Lys Ala Ala Ala Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide

<400> SEQUENCE: 3

Ala Lys Glu Tyr Ala Ala Ala Ala Ala Lys Ala Ala Ala Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide

<400> SEQUENCE: 4

Ala Lys Lys Tyr Ala Ala Ala Ala Ala Lys Ala Ala Ala Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide

<400> SEQUENCE: 5

Ala Glu Ala Tyr Ala Ala Ala Ala Ala Lys Ala Ala Ala Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Lys Glu Ala Tyr Ala Ala Ala Ala Ala Lys Ala Ala Ala Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Ala Glu Glu Tyr Ala Ala Ala Ala Ala Lys Ala Ala Ala Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

Ala Ala Glu Tyr Ala Ala Ala Ala Ala Lys Ala Ala Ala Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide

<400> SEQUENCE: 9

Glu Lys Ala Tyr Ala Ala Ala Ala Ala Lys Ala Ala Ala Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Ala Ala Lys Tyr Glu Ala Ala Ala Ala Lys Ala Ala Ala Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Ala Ala Lys Tyr Ala Glu Ala Ala Ala Lys Ala Ala Ala Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Glu Ala Ala Tyr Ala Ala Ala Ala Ala Lys Ala Ala Ala Ala

```
                    1               5                   10                  15
```

```
<210> SEQ ID NO 13
<211> LENGTH: 15
<212> TYPE: PRT
<213> ORGANISM: Artificial Sequence
<220> FEATURE:
<223> OTHER INFORMATION: Synthetic peptide

<400> SEQUENCE: 13

Glu Lys Lys Tyr Ala Ala Ala Ala Ala Lys Ala Ala Ala Ala Ala
 1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide

<400> SEQUENCE: 14

Glu Ala Lys Tyr Ala Ala Ala Ala Ala Lys Ala Ala Ala Ala Ala
 1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide

<400> SEQUENCE: 15

Ala Glu Lys Tyr Ala Ala Ala Ala Ala Ala Ala Ala Ala Ala Ala
 1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Ala Lys Glu Tyr Ala Ala Ala Ala Ala Ala Ala Ala Ala Ala Ala
 1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide

<400> SEQUENCE: 17

Ala Lys Lys Tyr Glu Ala Ala Ala Ala Ala Ala Ala Ala Ala Ala
 1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide

<400> SEQUENCE: 18

Ala Lys Lys Tyr Ala Glu Ala Ala Ala Ala Ala Ala Ala Ala Ala
 1               5                   10                  15
```

```
<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Ala Glu Ala Tyr Lys Ala Ala Ala Ala Ala Ala Ala Ala Ala Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide

<400> SEQUENCE: 20

Lys Glu Ala Tyr Ala Ala Ala Ala Ala Ala Ala Ala Ala Ala Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide

<400> SEQUENCE: 21

Ala Glu Glu Tyr Lys Ala Ala Ala Ala Ala Ala Ala Ala Ala Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide

<400> SEQUENCE: 22

Ala Ala Glu Tyr Lys Ala Ala Ala Ala Ala Ala Ala Ala Ala Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Glu Lys Ala Tyr Ala Ala Ala Ala Ala Ala Ala Ala Ala Ala Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

Ala Ala Lys Tyr Glu Ala Ala Ala Ala Ala Ala Ala Ala Ala Ala
1               5                   10                  15
```

```
<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Ala Ala Lys Tyr Ala Glu Ala Ala Ala Ala Ala Ala Ala Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide

<400> SEQUENCE: 26

Glu Lys Lys Tyr Ala Ala Ala Ala Ala Ala Ala Ala Ala Ala Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide

<400> SEQUENCE: 27

Glu Ala Lys Tyr Ala Ala Ala Ala Ala Ala Ala Ala Ala Ala Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide

<400> SEQUENCE: 28

Ala Glu Tyr Ala Lys Ala Ala Ala Ala Ala Ala Ala Ala Ala Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic peptide

<400> SEQUENCE: 29

Ala Glu Lys Ala Tyr Ala Ala Ala Ala Ala Ala Ala Ala Ala Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic peptide

<400> SEQUENCE: 30

Glu Lys Tyr Ala Ala Ala Ala Ala Ala Ala Ala Ala Ala Ala Ala
1               5                   10                  15
```

```
<210> SEQ ID NO 31
<211> LENGTH: 15
<212> TYPE: PRT
<213> ORGANISM: Artificial Sequence
<220> FEATURE:
<223> OTHER INFORMATION: Synthetic peptide

<400> SEQUENCE: 31

Ala Tyr Lys Ala Glu Ala Ala Ala Ala Ala Ala Ala Ala Ala Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic peptide

<400> SEQUENCE: 32

Ala Lys Tyr Ala Glu Ala Ala Ala Ala Ala Ala Ala Ala Ala Ala
1               5                   10                  15
```